(12) United States Patent
Ettema et al.

(10) Patent No.: US 6,242,460 B1
(45) Date of Patent: Jun. 5, 2001

(54) ZOLPIDEM SALT FORMS

(75) Inventors: Gerrit Jan Bouke Ettema, Denekamp; Jacobus Maria Lemmens, Mook; Theodorus Hendricus Antonius Peters, Arnhem, all of (NL); Frantisek Picha, Brno (CZ)

(73) Assignee: Synthon BV (NL)

( * ) Notice: Subject to any disclaimer, the term of this patent is extended or adjusted under 35 U.S.C. 154(b) by 0 days.

(21) Appl. No.: 09/449,974

(22) Filed: Nov. 26, 1999

Related U.S. Application Data
(60) Provisional application No. 60/126,494, filed on Mar. 25, 1999.

(51) Int. Cl.[7] .................................................... A61K 31/44
(52) U.S. Cl. ......................... 514/300; 546/121; 546/122
(58) Field of Search .................................. 546/121, 122; 514/300

(56) References Cited

U.S. PATENT DOCUMENTS

| 4,382,938 | 5/1983 | Kaplan et al. . |
|---|---|---|
| 4,794,185 | 12/1988 | Rossey et al. . |

FOREIGN PATENT DOCUMENTS

| 0 050 563 | 5/1984 | (EP) . |
|---|---|---|
| 0 251 859 | 11/1990 | (EP) . |

OTHER PUBLICATIONS

George et al., Zolpidem and Related Compounds: Syntheses, Physical Properties and Structure–Activity Relationships, 1988, pp. 11–23.

Schmitt et al., Imidazo[1,2–b]pyridazines. XXIII Some 5–Deaza Analogues. Syntheses of Some 2–Arl–6–(chloro, methoxy or unsubstituted) imidazo[1,2–a]pyridanes and Their Affinity for Central and Mitochondrial Benzodiazepine Receptors, 1997, pp. 719–725.

Trapani et al., Synthesis and Binding Affinity of 2–Phenylimidazo[1,2–a]pyridine Derivitives for both Central and Peripheral Benzodiazepine Receptors. A New Series of High–Affinity and Selective Ligands for the Peripheral Type, 1997, pp. 3109–3118.

*Primary Examiner*—Frederick Krass
*Assistant Examiner*—Donna Jagoe
(74) *Attorney, Agent, or Firm*—Mark R. Buscher

(57) ABSTRACT

Zolpidem salts having improved physical stability do not exhibit a melting endotherm corresponding to zolpidem free base when heated at 5° C./minute from about 25° C. to 250° C. The salts are generally easy to reproduce, even on an industrial scale and are easier to handle due to the increased stability than the known zolpidem tartrate. The zolpidem salts are typically pharmaceutically acceptable salts and can be used in formulating pharmaceutical compositions and in pharmaceutical uses; e.g. as a hypnotic.

30 Claims, 12 Drawing Sheets

ZOLPIDEM SALT FORMS

This application claims the benefit of priority under 35 U.S.C. 119 from prior U.S. provisional patent application No. 60/126,494, filed Mar. 25, 1999, the entire contents of which are incorporated herein by reference.

BACKGROUND OF THE INVENTION

1. Field of the Invention

The present invention relates to novel salt forms of zolpidem and to pharmaceutical compositions and methods of treatment containing the same.

2. Description of the Related Arts

Zolpidem is a known hypnotic agent having the following formula.

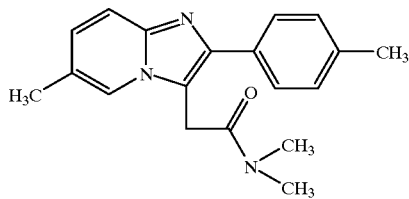

It has been marketed in solid dosage forms for peroral application (tablets) under the trade marks AMBIEN® and STILNOX®. As the active substance in these pharmaceutical dosage forms, zolpidem is present in the form of a salt with natural L(+)tartaric acid ((2R,3R)-2,3-dihydroxybutanedicarboxylic acid) wherein the molar ratio of zolpidem and tartaric acid in the salt is 2:1. This salt is conventionally called zolpidem hemitartrate but more a correct denomination thereof, which will be used hereinafter, is zolpidem tartrate.

The zolpidem free base was disclosed generically in EP 50563 of Synthelabo. The zolpidem tartrate used in the commercial products, along with an improved synthesis scheme, was subsequently disclosed in EP 251859 (U.S. Pat. No. 4,794,185). It is believed that the process set forth in this patent corresponds to the commercial process presently used for the production of zolpidem. An example therein shows the production of zolpidem and the formation of the tartrate salt. Specifically, 25 g of zolpidem free base is dissolved in 180 ml of methanol and combined with 60 ml of a methanol solution containing 6.1 g of tartaric acid (a 1:2 molar ratio) and then allowing the mixed solution to crystallize. The crystalline product is reported to have a melting point of 197° C. The specific details of how the crystallization is performed are not disclosed.

The European Pharmacopoeia, Monograph No. 1999:1280, states that zolpidem tartrate is characterized as a white or almost white crystalline powder, hygroscopic, slightly soluble in water, sparingly soluble in methanol, and practically insoluble in methylene chloride. For identification purposes, a Pharmacopoeial reference standard, namely zolpidem tartrate CRS, is a commercially available substance that serves as the reference for any analysis or comparison.

The crystal structure of the zolpidem tartrate has also been published in an article of P. George et al. (Zolpidem and related compounds, in: Imidazopyridines in Sleep Disorders, edited by J. P. Sauvanet et al., Raven Press New York 1988, p. 11 ff.), the entire contents of which is incorporated herein by reference. When interpreting the results of single crystal X-ray structure analysis, it was concluded by the above authors that the crystal lattice repeating unit contained two layers of zolpidem, one protonated (and thus ionically bound to the tartaric acid moiety) and one unprotonated (and thus bound by other than ionic bonding).

However, studies conducted by the present inventors have revealed that forming the zolpidem tartrate salt is difficult. The method of manufacturing zolpidem tartrate described in the documents discussed above comprises crystallization of a mixed solution of zolpidem free base and tartaric acid (in 2:1 molar ratio) in methanol. The present inventors repeated this method with the aim to test the ruggedness of the production method in modeling situations encountered on an industrial scale (changes in temperature regimen, concentration of components, quality of solvent used, etc.) and found out that the crystallization process is highly irreproducible. Proper formation of crystalline zolpidem tartrate in desired yield and quality is highly dependent on strict control and maintaining the optimum crystallization conditions, quality of starting materials (namely content of water in methanol) and molar ratio of zolpidem and tartaric acid. It often happened that, from batch to batch and under otherwise the same conditions, crystals were not formed at the preselected temperature in a reasonable time and it was necessary to continue with cooling the mixture to lower temperatures to obtain a solid product. At temperatures lower than ambient, impurities present in the starting materials can also coprecipitate and thus decrease the quality of the obtained product. Also, and sometimes unpredictably, another salt is obtained instead of the desired tartrate. Thus, it is highly unpredictable to estimate whether and when the desired product will be obtained from the solution and what the yield and quality of the product from a production batch will be.

Moreover, the present inventors have found that the known zolpidem tartrate has low physical stability. That is, the application of energy such as mechanical grinding, heat, etc., to the known zolpidem tartrate can readily cause the crystal structure to change forms and in particular can cause the release of zolpidem free base. In retrospect, the instability of the zolpidem tartrate makes sense in view of the unprotonated zolpidem layer within the crystal lattice and the fact that zolpidem is a very weak base. This physical instability can lead to unintended changes in the zolpidem salt form during manufacture or storage. For example, during storage the zolpidem tartrate could begin to decompose into a mixture of zolpidem hydrogen tartrate (1:1 ratio of zolpidem to tartaric acid) and zolpidem free base. The zolpidem free base is not as water soluble as the zolpidem tartrate or zolpidem hydrogen tartrate and thus may not be taken up by the body in vivo thereby reducing the bioavailability.

Accordingly, it would be desirable to have a zolpidem salt form that exhibits greater physical stability than the known zolpidem tartrate. It would also be desirable to have a zolpidem salt form that is readily reproducible, especially on an industrial scale.

SUMMARY OF THE INVENTION

The present invention relates to a solid-phase zolpidem salt form having sufficient physical stability that upon heating from about 20° C. to about 250° C. at a rate of about 5° C./minute does not exhibit a melting endotherm that corresponds to zolpidem free base. The present invention is generally based on the discovery that by forming zolpidem salts that avoid a large amount of unprotonated zolpidem moieties, a zolpidem salt form can be obtained that exhibits superior physical stability in comparison to the known zolpidem tartrate salt form. For example, the salt form according to the present invention will typically exhibit a single melting endotherm when heated. In contrast, the prior zolpidem tartrate form will exhibit two melting endotherms: one for the zolpidem hydrogentartrate and one for the zolpidem free base that was released during the heating process.

One way to avoid having a large number of unprotonated zolpidem moieties in the salt is by having a molar ratio of zolpidem moiety to anion in the range of about 0.9–1.35:1, more preferably about 1:1. Such salts represent another aspect of the present invention. The salts can be made from pharmaceutically acceptable acid addition salts such as hydrochloride, hydrobromide, maleate, fumarate, tartrate, sulfate and sulfonates.

The salt forms may be crystalline or amorphous and they may contain bound water or solvent or be substantially free of the same. Preferred salts include various forms of zolpidem hydrogentartrate, zolpidem hydrochloride, and zolpidem methane sulfonate. The invention also relates to the use of the physically stable zolpidem salts of the present invention as intermediates in the preparation of a zolpidem salt including the known zolpidem tartrate.

The zolpidem salt forms of the present invention are useful in pharmaceutical compositions and for the treatment of mammals such as for inducing sleep or drowsiness. The pharmaceutical compositions can be solid dosage forms or liquid dosage forms containing the zolpidem salt dissolved therein.

DETAILED DESCRIPTION OF THE INVENTION

Figure 1:
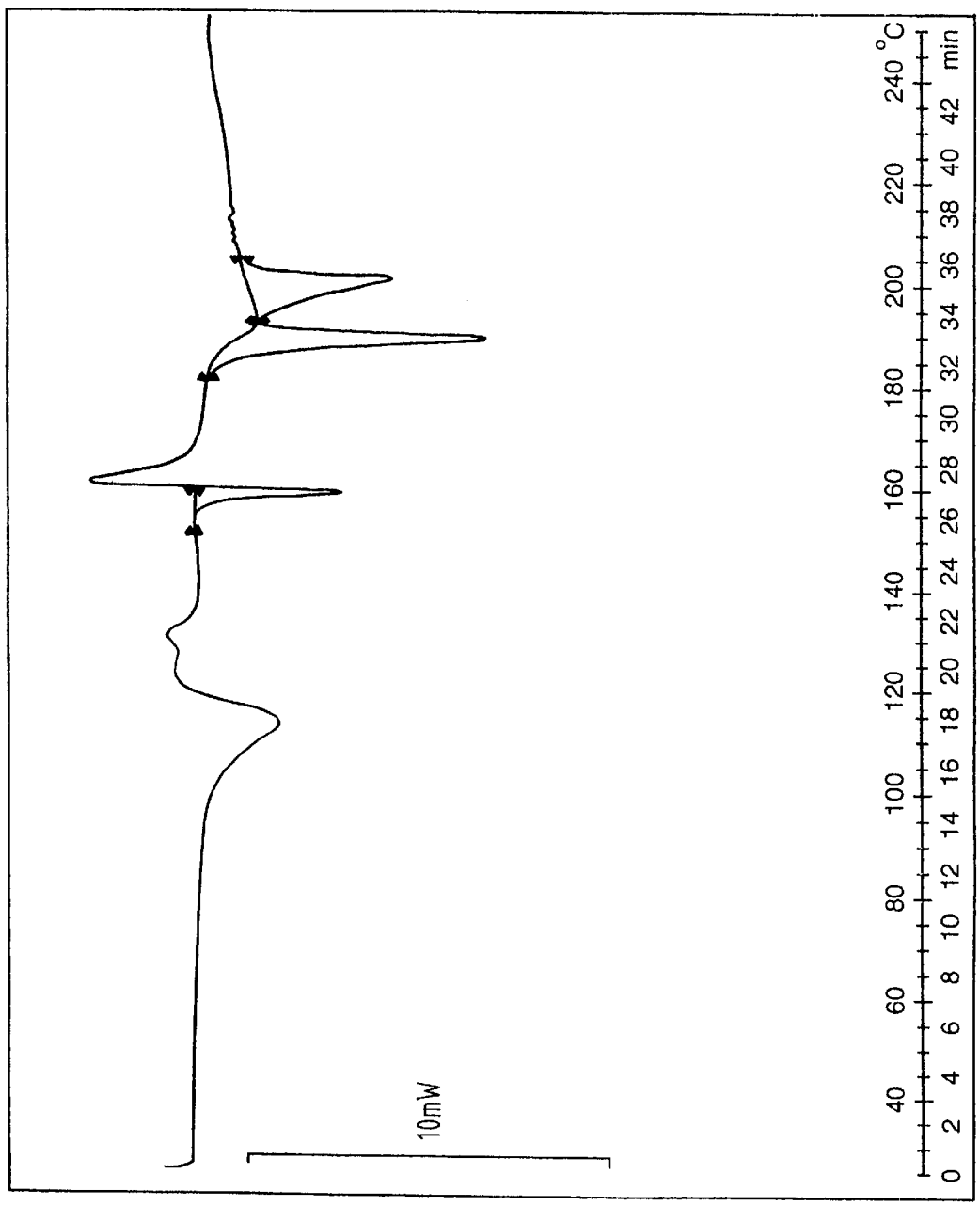
FIG. 1 shows a DCS curve of standard zolpidem tartrate.

The present invention relates to solid-phase zolpidem salt forms that exhibit improved physical stability. Specifically, upon heating from about 20° C. to about 250° C. at a rate of about 5° C./minute, none of the zolpidem salt forms of the present invention will exhibit a melting endotherm that corresponds to zolpidem free base. In practice this means that the zolpidem salt form does not disproportionate due to the application of heat to liberate a zolpidem free base prior to melting. Instead, the zolpidem salts of the present invention are thermally stable; i.e. no appreciable liberation of a zolpidem free base. The above heating test is usually carried out in a differential scanning calorimeter (DSC) under a nitrogen atmosphere at atmospheric pressure. Alternatively, the heating test may be performed using differential thermal analysis (DTA).

To determine whether a melting endotherm corresponds to the melting of a zolpidem free base fraction within the composition, a sample of the same test composition is run again but this time with zolpidem free base added and admixed therein. If the melting endotherm originally observed in the first test is larger, then the endotherm corresponds to the melting of zolpidem free base. Alternatively, if a different melting endotherm is induced by the artificial introduction of zolpidem free base, then the original melting endotherm does not correspond to the zolpidem free base. For clarity, "melting endotherms," as is understood in the art, are those endotherms where the operator of the DSC visually observes that the sample is melting.

Normally the zolpidem salt forms of the present invention exhibit only one melting endotherm. However, it is possible that a salt form will have two or more melting endotherms and still not release a free base of zolpidem. For instance, the salt form may melt and recrystallize as a new crystal and then melt again, but without releasing the zolpidem free base. Such a composition would have two melting endothermns but neither of them would correspond to a melting endotherm for zolpidem free base. In contrast, the conventional zolpidem tartrate exhibits two melting endotherms because the composition is not thermally stable and during the heating process is converted into a mixture of zolpidem hydrogen tartrate and zolpidem free base. The first melting endotherm corresponds to zolpidem free base while the second corresponds to zolpidem hydrogentartrate.

The zolpidem salts of the present invention generally display good physical stability to a variety of energy inputs. For example, beyond the above prescribed heating test, the inventive salts are generally stable against a variety of heat treatments including long term exposure to constant low level heating. The same is not true of the conventional zolpidem tartrate. Similarly, the zolpidem salts of the present invention are generally physically stable to ultrasound exposure and mechanical stresses such as grinding and compression. That is, after being subjected to these treatments, a zolpidem free base is not appreciably released. Zolpidem free base is considered to be "appreciably released" or appreciably present in the composition when the zolpidem free base provides a visually discernable peak on an IR, DSC, or x-ray powder diffraction graph. Generally a peak is not visually discernable when the amount of zolpidem free base is less than 2% and preferably less than 1% of the zolpidem moieties present in the composition.

In contrast to the present invention, the application of energy to the known zolpidem tartrate such as by heating results in a composition that is different from zolpidem tartrate but indistinguishable from an artificially made admixture of zolpidem hydrogentartrate and zolpidem free base in terms of IR and X-ray powder diffraction. Surprisingly, the same solid-state decomposition has been observed when zolpidem tartrate was subjected to milling, long-term drying or by an action of ultrasound even at temperatures close to ambient. Examination of such treated zolpidem tartrate by IR spectrum or X-ray powder diffraction analysis, shows that the product turned, at least partly, into the physical mixture of zolpidem free base and zolpidem hydrogentartrate. The same behavior could be expected during the tabletting process wherein local overheating is commonly encountered during the homogenization and/or compression (pressurization) of the tablet composition. Indeed, the tabletting process is one of the most common reasons for decomposition of sensitive compounds in the final dosage form.

The stability of the present salt form can be attained by avoiding the weaknesses of the known zolpidem tartrate. Specifically, the presence of a layer of unprotonated zolpidem and/or the presence of methanol as a solvate should be avoided. The unprotonated zolpidem is only weakly bound to the lattice. Accordingly, this zolpidem molecule is susceptible to being released from the crystal lattice without much energy being applied. Avoiding the formation of a salt form where a zolpidem is unprotonated will generally increase the physical stability of the salt form so as to conform with the present invention.

Regarding the methanol solvate, it has now been discovered that methanol plays a very important role in forming the conventional zolpidem tartrate. Surprisingly, in trying to prepare zolpidem tartrate by crystallization, using a 2:1 molar ratio of zolpidem and tartaric acid and employing non-methanolic solvents such as ethanol, isopropanol and acetone, results in no zolpidem tartrate. Instead, only zolpidem hydrogentartrate is obtainable. This salt has not been described heretofore and is discussed in more detail hereinafter. Analysis of freshly prepared zolpidem tartrate indicates that it is in fact a solvate with methanol. Two molecules of methanol per one molecule of zolpidem tartrate are present herein. This was confirmed by repeating the x-ray analysis on a single crystal of zolpidem tartrate obtained by crystallization from methanol according to the disclosed method in the George et al article cited above. Methanol, it seems, is a crucial partner to zolpidem and tartaric acid molecules in the process of crystallization and forming the crystalline lattice of the known zolpidem tartrate. Only in its presence is the crystalline lattice with the orientation having protonated and unprotonated zolpidem and tartaric acid units arranged in parallel layers formed.

The methanol can be removed from the lattice, at least in part, by conventional drying or by prolonged storage at ambient temperatures. Once methanol leaves, the lattice becomes quite sensitive and is readily disturbed by the application of energy resulting in the breakdown of the lattice and the release of zolpidem free base.

In non-methanolic solvents, the molecule of solvent is probably too large to be included into such an oriented crystalline lattice and thus the crystals of zolpidem tartrate are not formed. Also, it appears that the water and/or impurities present in methanol play a role in forming the crystalline lattice. This may also explain the unexpected failures in producing zolpidem tartrate as, instead, zolpidem hydrogentratrate has been sometimes obtainable from methanol, even when using a proper 2:1 molar ratio.

The solid-phase zolpidem salt forms of the present invention may be crystalline or amorphous. Generally, the ratio of zolpidem to anion is significantly less than 2:1 in the salt form, such as within the range of 0.9–1.35:1, more typically around 1:1. The anion preferably forms a pharmaceutically acceptable salt, although other salts are contemplated as intermediates or for use in purification, etc. Typically the anion is a pharmaceutically acceptable acid addition salt. Examples of suitable salts include hydrochloride, hydrobromide, maleate, fumarate, tartrate, sulfate and sulfonates such as mesylate and tosylate. The salt can be formed by combining a zolpidem source and an anion source in a solvent to form a solution that contains at least one of the zolpidem and the anion source dissolved therein; and recovering a solid zolpidem salt from the solution. The solvent is typically an alcohol, ketone, hydrocarbon, chlorinated hydrocarbon or water. The zolpidem source is usually a zolpidem free base although other sources such as salts or precursors thereof can also be used. The anion source is generally a pharmaceutically acceptable acid, preferably an acid selected from the group consisting of HCl, HBr, maleic acid, fumaric acid, tartaric acid, and alkyl- or aryl-sulfonic acid. However, when the zolpidem source is zolpidem free base and the anion source is tartaric acid, it is preferable that methanol is not the solvent. More generally, when the zolpidem source is zolpidem free base, it is usually desirable that a non-methanolic solvent be used. The recovery step can be carried out by crystallization, with or without ultrasound, freeze drying, spray drying or other known methods.

Certain preferred salts of the present invention are discussed in more detail below. Salts made from tartaric acid can be formed that exhibit physical stability such that a zolpidem free base is not released. Typically these salts are crystalline although amorphous forms can also be made. A salt having a zolpidem to tartaric acid molar ratio of 1:1 is zolpidem hydrogentartrate. In a preferred aspect, the zolpidem hydrogentartrate exists in a crystalline form and more preferably having the following characteristics:

m.p.: 203–204° C.

Figure 4:
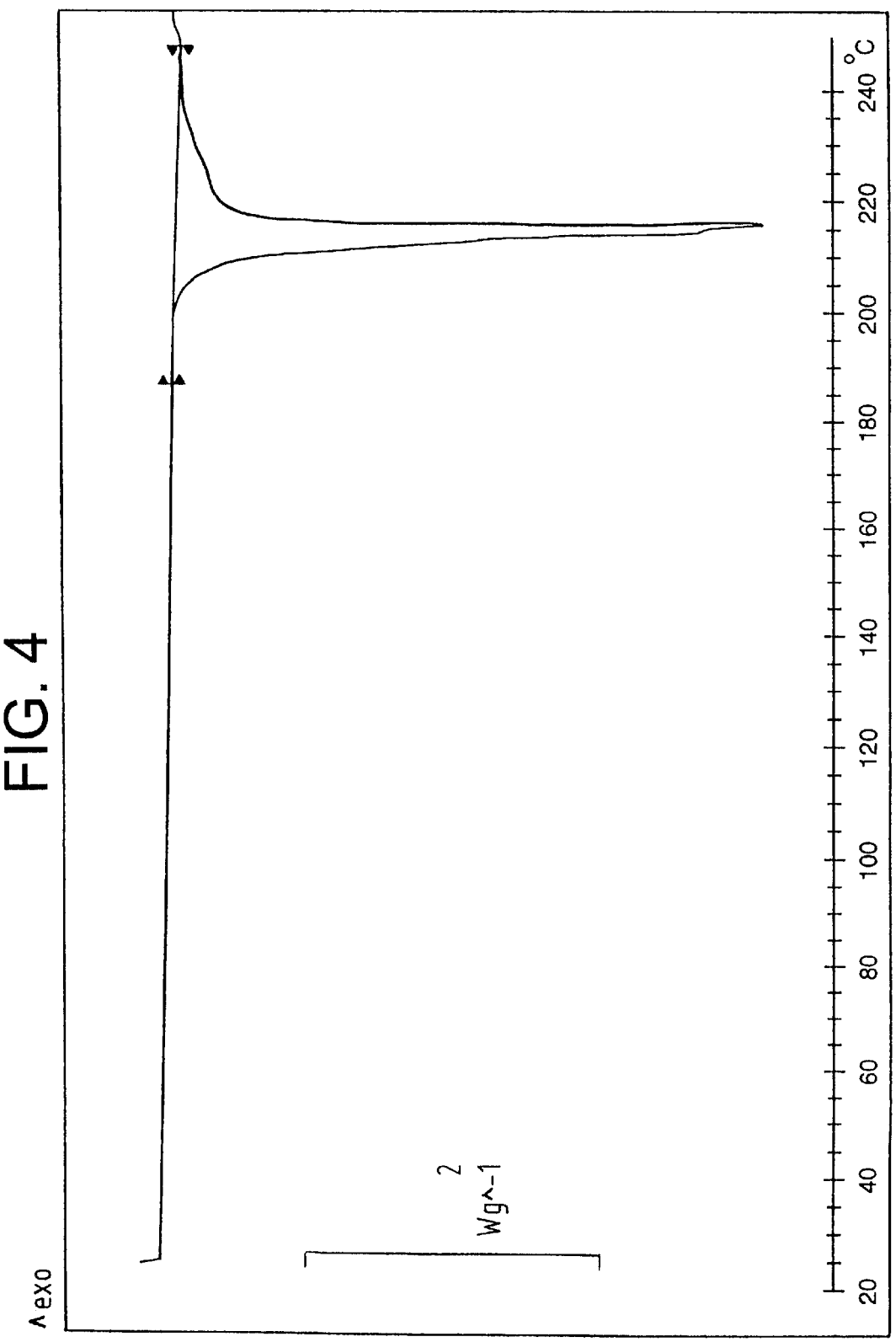
FIG. 4 shows a DSC curve of zolpidem hydrogentartrate.

DSC (5° C./min): single melting exotherm at around 203–204° C. as shown in FIG. 4.

Figure 5:
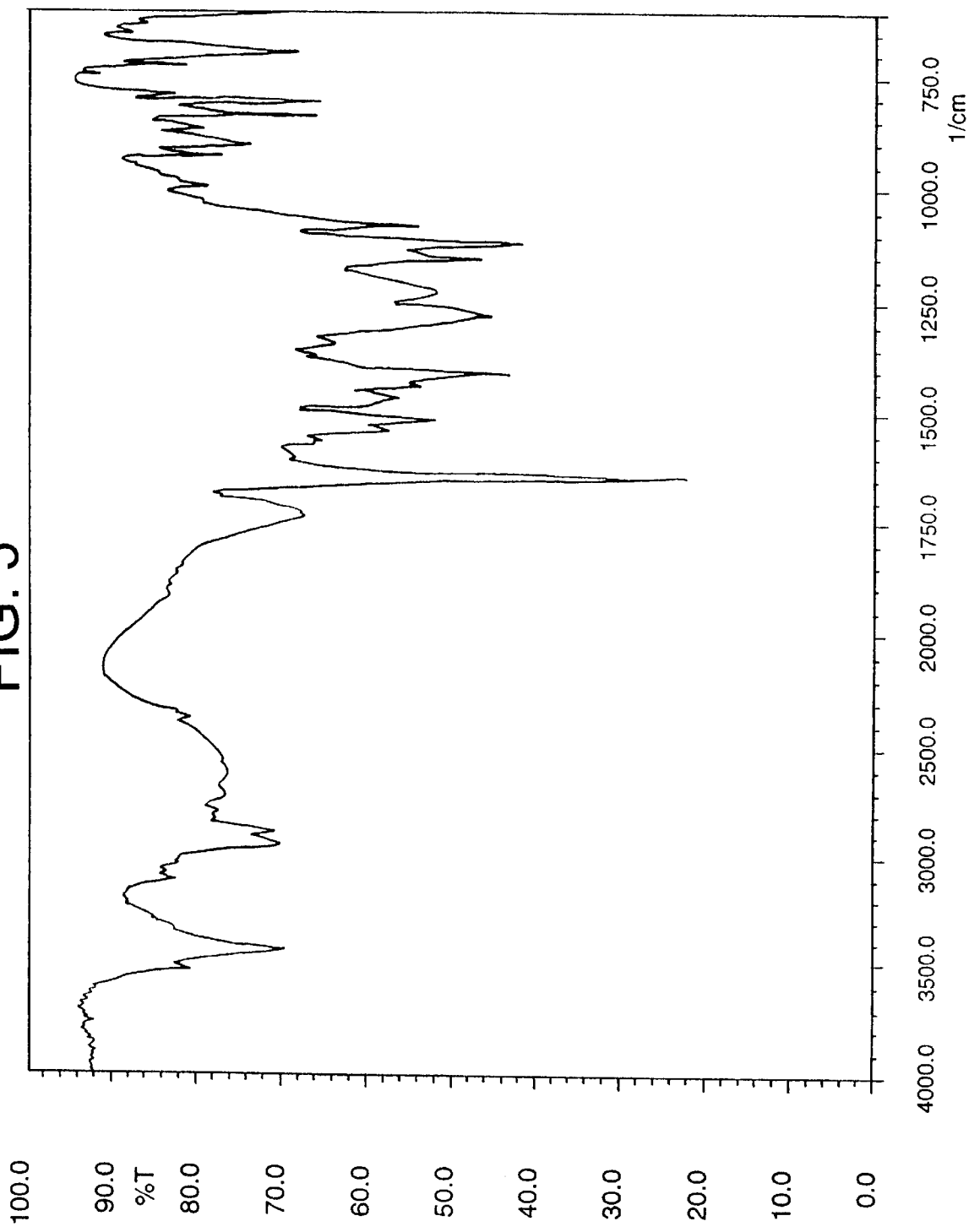
FIG. 5 shows an IR spectrum of zolpidem hydrogentartrate.

IR (KBr): as shown in FIG. 5.

Figure 6:
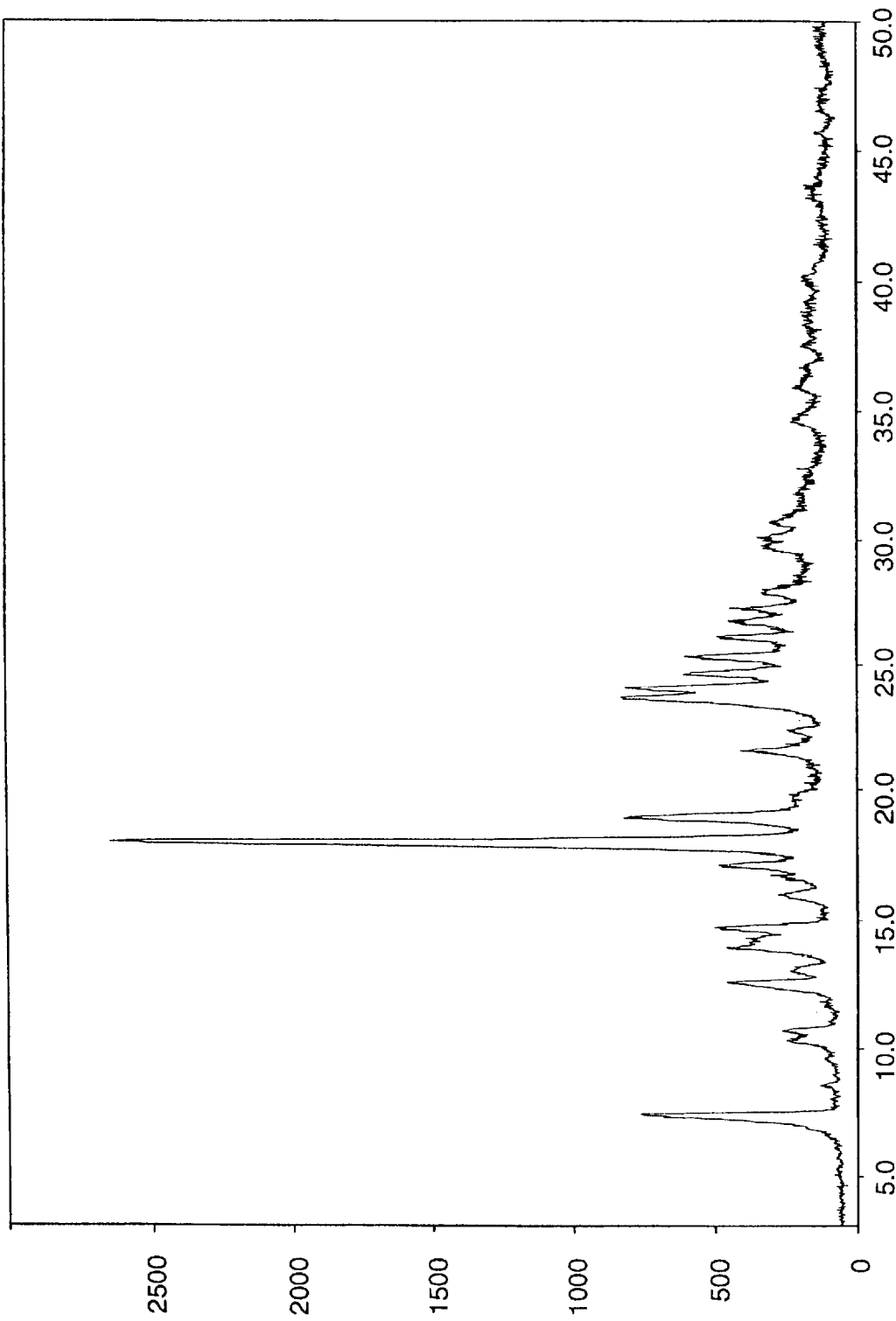
FIG. 6 shows an x-ray powder diffraction pattern of zolpidem hydrogentartrate.

X-ray powder diffraction: as shown in FIG. 6.

A product that substantially consists of this zolpidem hydrogentartrate crystalline salt can be prepared in reproducible manner and in industrial scale as will be shown herein below. The words "substantially consists" as used above mean that the content of the zolpidem hydrogentartrate in the isolated product is more than 95% pure, preferably more than 98% pure. This purity is advantageous in as much as the intended use of the product is as a pharmaceutically active agent.

It is preferred that the above product is produced substantially free from the bound solvent; i.e. less than 5% preferably less than 2% and more preferably less than 1% solvent. However, the product may be hydrated in to a limited extent as it may absorb water after prolonged standing under environment of higher humidity. Preferably, the product contains less than 3% of water. Water and/or bound solvents arising from production may be removed by conventional drying and the resulted product is still stable towards changes in crystalline structure after heating.

The zolpidem hydrogentartrate can be formed when mixing zolpidem free base and tartaric acid in the appropriate solvent such as ethanol, acetone or isopropanol, preferably in amounts close to theoretical (1:1 molar ratio) but it is also formed when mixing zolpidem free base with an excess of tartaric acid (e.g. up to 1:3 molar ratio) or deficiency of tartaric acid (e.g. up to 3:1 molar ratio). Generally, any of solvents in which both zolpidem and tartaric acid are at least partly soluble is a suitable solvent, and in reality so long as at least one of the zolpidem or tartaric acid is partly soluble in the solvent, salt formation can proceed, albeit much more slowly.

This also illustrates advantages in preparation of crystalline zolpidem hydrogentartrate of the invention as it may be formed under conditions that do not require careful control of crystallization conditions, quality of solvents, quality of the starting materials and their mutual ratio. The compound may thus be produced in a reproducible manner with reliable results in industrial scale.

Although the zolpidem hydrogentartrate is conventionally formed as a crystal, an amorphous form can also be made. Specifically, by subjecting the above crystalline zolpidem hydrogentartrate to freeze drying from a water solution, a different form of zolpidem hydrogen tartrate is obtained. This form has the same chemical composition as the starting zolpidem hydrogentartrate but it has no defined x-ray powder diffractogram and it is thus an amorphous zolpidem hydrogentartrate. Physical stability in solid state is the same for the amorphous form as in the case of crystalline compound.

Amorphous zolpidem hydrogentartrate is formed as microparticulate solid matter with low bulk density so that it dissolves rapidly and reliably in pharmaceutically acceptable solvents (carriers or diluents) such as water or physiological saline. According the amorphous form is useful in formulating liquid dosage forms such as for injections.

In addition to zolpidem hydrogentartrate, other tartrate salts can be formed by controlling the salt formation conditions. For example, forms having a ratio other than 1:1 can be made including salt form where the molar ratio of zolpidem to anion is 4:3 (or 1.33:1).

Another preferred salt of the present invention is zolpidem hydrochloride. This salt may be formed in several crystalline forms in dependence on the method of salt formation. However, all the modifications described below fall under the scope of the invention, i.e. they do not decompose into zolpidem free base and hydrochloric acid under action of energy.

Crystalline zolpidem hydrochloride monohydrate may be obtained by crystallization of an equimolar mixture of zolpidem and concentrated hydrochloric acid from their solution in acetone. The melting point of the product when determined on Koffler block is around 277° C. The DCS curve shows that this salt form releases water at approximately 120° C. to form an anhydrous zolpidem hydrochloride, which then has a single melting endotherm at 282° C. The content of water corresponds to one molar equivalent and, as apparent from the elevated release temperature, water is bound in the crystalline lattice quite firmly.

Anhydrous crystalline zolpidem hydrochloride may be obtained by crystallization from n-butanol. This salt form exhibits a single melting endotherm on DSC at 282° C. and the melting point, in accordance with the above comment to the monohydrate, is also around 277° C.

When crystallizing zolpidem hydrochloride from an ethanolic solution, a compound is obtained which has yet another peak on DSC at approximately 86° C. Chemical analysis reveals that the produced salt form is a solvate with the ethanol content corresponding to a half molar equivalent. Thus, the product can be characterized as zolpidem hydrochloride hemiethanolate. The melting endotherm on DSC is, similarly as above, approximately 282° C. which indicates that, after liberating ethanol, this salt form also melts without decomposition into zolpidem free base.

Another form of zolpidem hydrochloride may be prepared by passing hydrogen gas through a solution of zolpidem free base in a suitable solvent. In this case, even less polar solvents, such as dichloromethane, may be suitably employed.

Amorphous zolpidem hydrochloride may be prepared by dissolution of a crystalline salt form such as any of the above salt forms, in water and freeze drying of the resulting solution.

Another advantageous salt form of the present invention are zolpidem sulfonates, especially methane sulfonate salt or mesylate. In general these salt forms may be prepared by dissolving zolpidem and methane sulfonic acid (or other alkyl- or aryl-sulfonic acid) in methanol, evaporating the solvent to dryness and crystallization of the resulting mixture from acetone. Zolpidem methane sulfonate exhibits on DSC curve a single melting enotherm at 206° C. Similarly, zolpidem p-toluene sulfonate may be prepared which exhibits a single melting endotherm at 219° C.

In the production of the zolpidem salts of the present invention, starting zolpidem may be obtained by synthetic methods described in the prior art e.g. in EP 50563 and EP 251859 and also by the methods described in commonly owned U.S. patent application Ser. No. 60/126,494.

All the above described inventive zolpidem salt forms are useful as pharmaceuticals in the same therapeutic category as the known zolpidem tartrate and they can be formulated into conventional pharmaceutical dosage forms. In particular, zolpidem salt forms can be used as hypnotics to aid in sleep disorders or in any application where sleep or drowsiness is desired. More recently, zolpidem has been suggested for use in treating Parkinson's disease, parkinsonian symptoms, obsessive-compulsive disorder and certain dementias in U.S Pat. No. 5,891,891, the entire contents of which are incorporated herein by reference. The zolpidem salts can be administered in dosage forms and routes well known in the art. Generally, the pharmaceutical composition comprises a pharmaceutically acceptable carrier or diluent and an effective amount, e.g. a hypnotically effective amount, of one of the above described novel zolpidem salt forms. The amount of zolpidem tartrate that is effective for a given condition or treatment is well known in the art and/or can be readily ascertained by workers skilled in the art. Generally the zolpidem salt form is contained in an amount within the range from about 5 mg to 50 mg per unit dose. The dosage forms include solid as well as liquid and can be oral or parenteral. In one embodiment the composition comprises a pharmaceutically acceptable liquid carrier having an effective hypnotic amount of the zolpidem salt according to the present invention dissolved therein. This composition can be either for oral administration or for injection. The liquid carrier is preferably water or ethanol or a combination thereof. Preferably, the composition is a tablet, a capsule, or a liquid. Preferred salts include zolpidem hydrogentartrate, zolpidem hydrochloride, zolpidem mesylate, zolpidem tosylate, and zolpidem sulfate, and more particularly amorphous zolpidem hydrogentartrate, crystalline zolpidem hydrogentartrate anhydrate, amorphous zolpidem hydrochloride, crystalline zolpidem hydrochloride monohydrate, crystalline zolpidem hydrochloride anhydrate, crystalline zolpidem hydrochloride hemiethanoate, crystalline zolpidem sulfate, and crystalline zolpidem mesylate.

A typical tablet formulation may contain zolpidem hydrochloride monohydrate, lactose, microcrystalline cellulose, hypromellose, carboxymethylstarch sodium and magnesium stearate. The tablets may be coated by conventional coating techniques.

Further, zolpidem salts, especially those that have good water solubility can be formulated into parenteral pharmaceutical dosage forms such as injectable compositions. Such injections should preferably consist of a sterile aqueous solution of the corresponding salt of zolpidem, with or without common excipients such as sodium chloride to avoid haemolysis and a physiologically acceptable buffer. In the following table, the solubility of zolpidem and various salts thereof in water at 20° C. are given in mg/ml:
Zolpidem 0.13
Zolpidem tartrate 18.8
Zolpidem hydrogentartrate 19.9
Zolpidem tosylate 22.2
Zolpidem hydrochloride monohydrate 110.0
Zolpidem sulfate 150.4
Zolpidem mesylate 432.0

It is apparent, zolpidem hydrochloride, sulfate, and mesylate (methane sulfonate) are examples of salts which are easy to be formulated into liquid parenteral forms and are preferred for use in such applications.

The dosage amounts of the active substance in the said pharmaceutical compositions and useful therapeutical regimens should advantageously correspond to the already recommended amounts and regiments of the known zolpidem tartrate but they are not limited thereto. The zolpidem salt form can be administered in an effective amount, by any of the above-described or known means, to an animal, particularly to a mammal in an effective hypnotic amount; i.e. effective to induce unconsciousness or drowsiness and preferably unconsciousness.

Beyond the pharmaceutical application, zolpidem salt forms according to the present invention, especially zolpidem hydrogentartrate, can also be used as intermediates in the formation of other or known salts of zolpidem. In particular, the known zolpidem tartrate can be made by a process that comprises combining zolpidem hydrogentartrate with a zolpidem free base in molar ratio of 1:1 in methanol to form a methanolic solution having a temperature of at least 50° C. and then cooling the methanolic solution to precipitate solid zolpidem tartrate. Further, an amorphous form of zolpidem tartrate can be made by mixing of zolpidem hydrogentartrate, either in solid form or in solution, with zolpidem free base in a proper solvent such as water or alcoholic solvent in a molar ratio 1:1 and separating the solid product by freeze drying and/or spray drying. The amorphous zolpidem tartrate possesses advantageous properties to that of the known crystalline form as it is formed in microparticulate form which has low bulk density. Therefore it dissolves more quickly in water, physiological saline, alcohol and similar pharmaceutically acceptable solvents and this fact is advantageous namely for industrial production of liquid pharmaceutical dosage forms. In oral pharmaceutical formulations such as tablets, it dissolves more rapidly than the crystalline compound so it may provide better bioavailability after peroral administration. The disadvantage of amorphous zolpidem tartrate is that it is formed as voluminous fluffy powder which is difficult to be handled.

More generally, all of the zolpidem salts of the present invention can be used as intermediates in the formation of another zolpidem salt. By forming a zolpidem salt of the present invention, especially a salt that is easily crystallizable, a more pure zolpidem product can be obtained. The salt formed in the crystallization can be converted to another salt directly or by first liberating zolpidem free base followed by salt formation. Such an intermediate crystallization process step represents an efficient method of purification of either a zolpidem free base or a zolpidem salt. Accordingly, any salt of the present invention is also useful in the preparation of another salt of zolpidem.

The following non-limiting examples are provided in order to further illustrate the present invention.

EXAMPLES

Example 1

Reference

Figure 2:
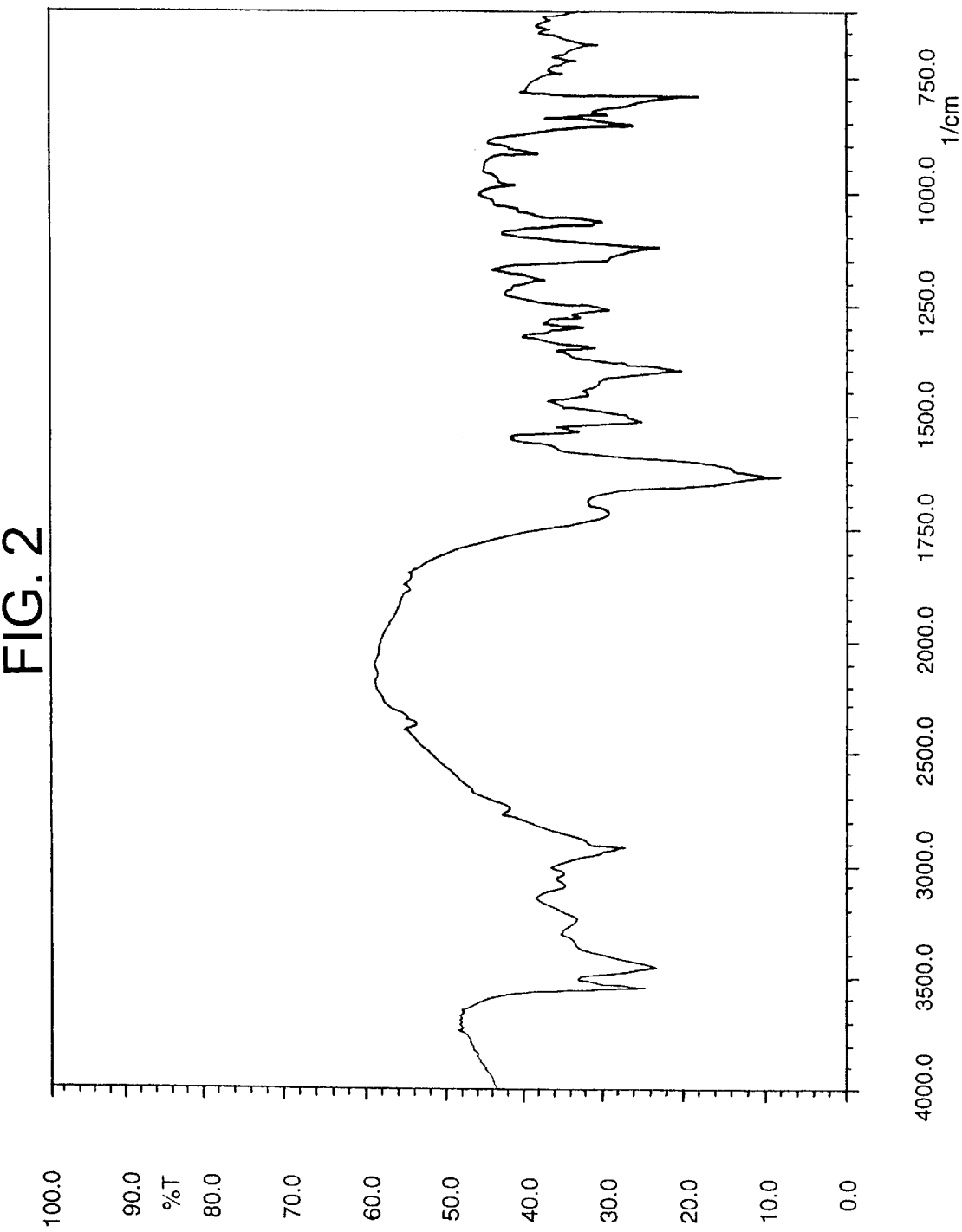
FIG. 2 shows an IR spectrum is the IR spectrum of standard zolpidem tartrate.
Figure 3:
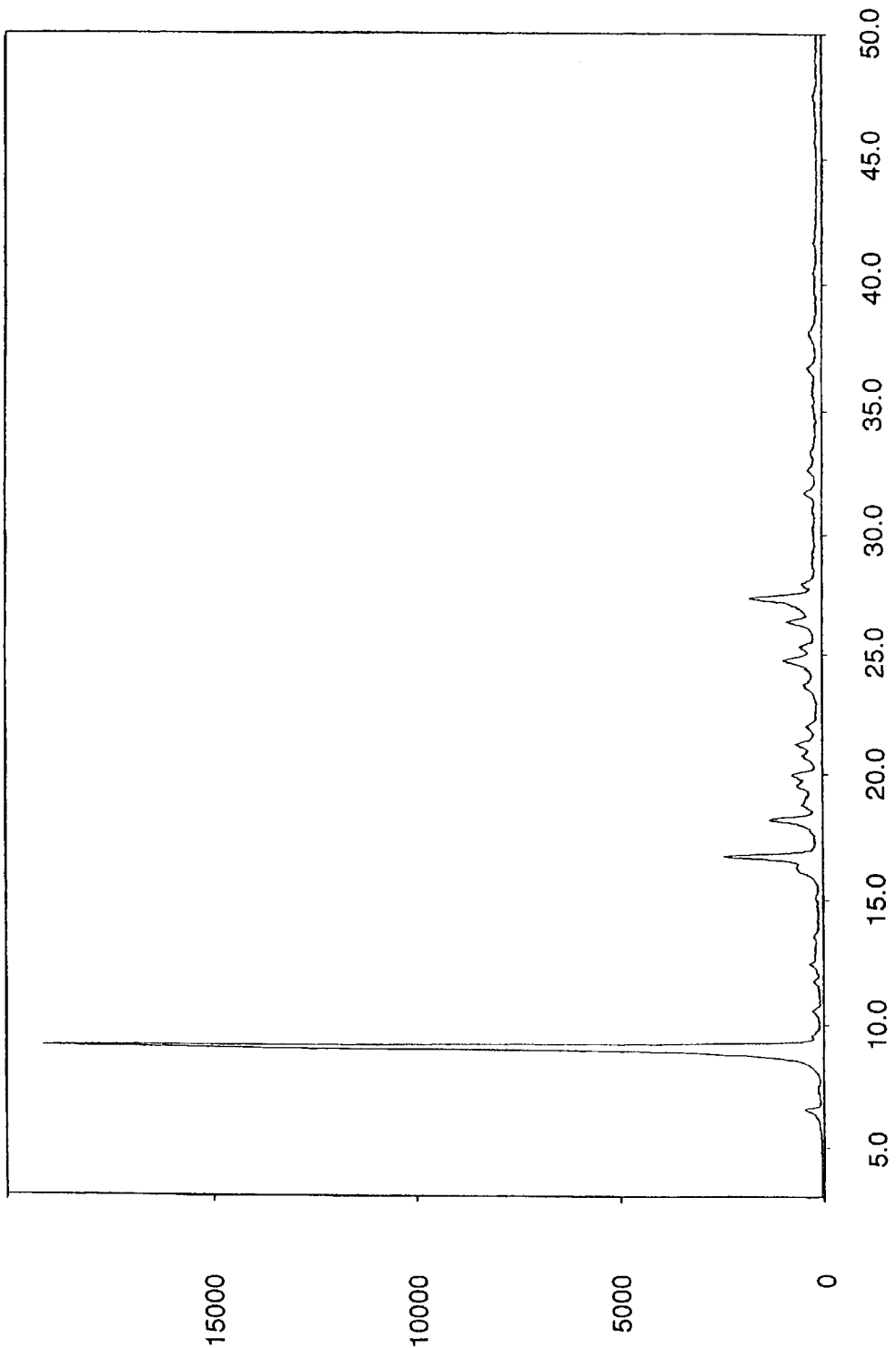
FIG. 3 shows an x-ray powder diffraction pattern of standard zolpidem tartrate.

A sample of the European standard for zolpidem tartrate (CRS) is obtained and subjected to DSC analysis, IR spectroscopy, and x-ray powder diffraction using conventional and/or standard methods and techniques. Representative results for the DSC, IR and x-ray powder diffraction are set forth in FIGS. 1, 2 and 3, respectively.

Example 2

Reference

A solution of 1 g (3.25 mmol) of zolpidem in 10 ml of methanol is prepared at room temperature. A second solution of 0.244 g (1.625 mmol) of tartaric acid is prepared at 50° C. Both solutions are mixed together at 50° C. under stirring and the clear mixture is kept at room temperature for 6 hours. No crystals are formed. The solution is stored at 4° C. overnight, and still no crystals are formed. The solution is kept at −20° C. for 2 hours resulting in crystal formation. The formed crystals are filtered off and washed with ether. DSC, IR and x-ray powder diffraction analyses return the same results as FIGS. 1–3, indicating that the product corresponds with zolpidem tartrate CRS (European Pharmacopoeia, 3rd Ed.).

Example 3

Crystalline Zolpidem Hydrogentartrate

In a 100 ml flask, 1 g of zolpidem is dissolved in 20 ml of isopropanol under heating. In another flask, 0.244 g of tartaric acid is dissolved in 10 ml of isopropanol while heating. The hot solutions are combined under stirring and the clear solution is allowed to stand at room temperature. After 30 minutes, crystallization starts spontaneously. After standing overnight at room temperature, the formed crystals are filtered off and washed by ether. NMR Spectrum of the product reveals that it is zolpidem hydrogentartrate. Representative DSC, IR and x-ray powder diffraction graphs are shown in FIGS. 4, 5, and 6, respectively.

Example 4

Crystalline Zolpidem Hydrogentartrate

Under stirring, 15 ml of anhydrous methanol is heated at reflux and 1 g of zolpidem and 0.244g of tartaric acid are added while hot. The resulting solution is left to cool at room temperature overnight. The formed crystals are filtered off and dried. The product is identical to the crystalline zolpidem hydrogentartrate produced in Example 3.

Example 5

Figure 7:
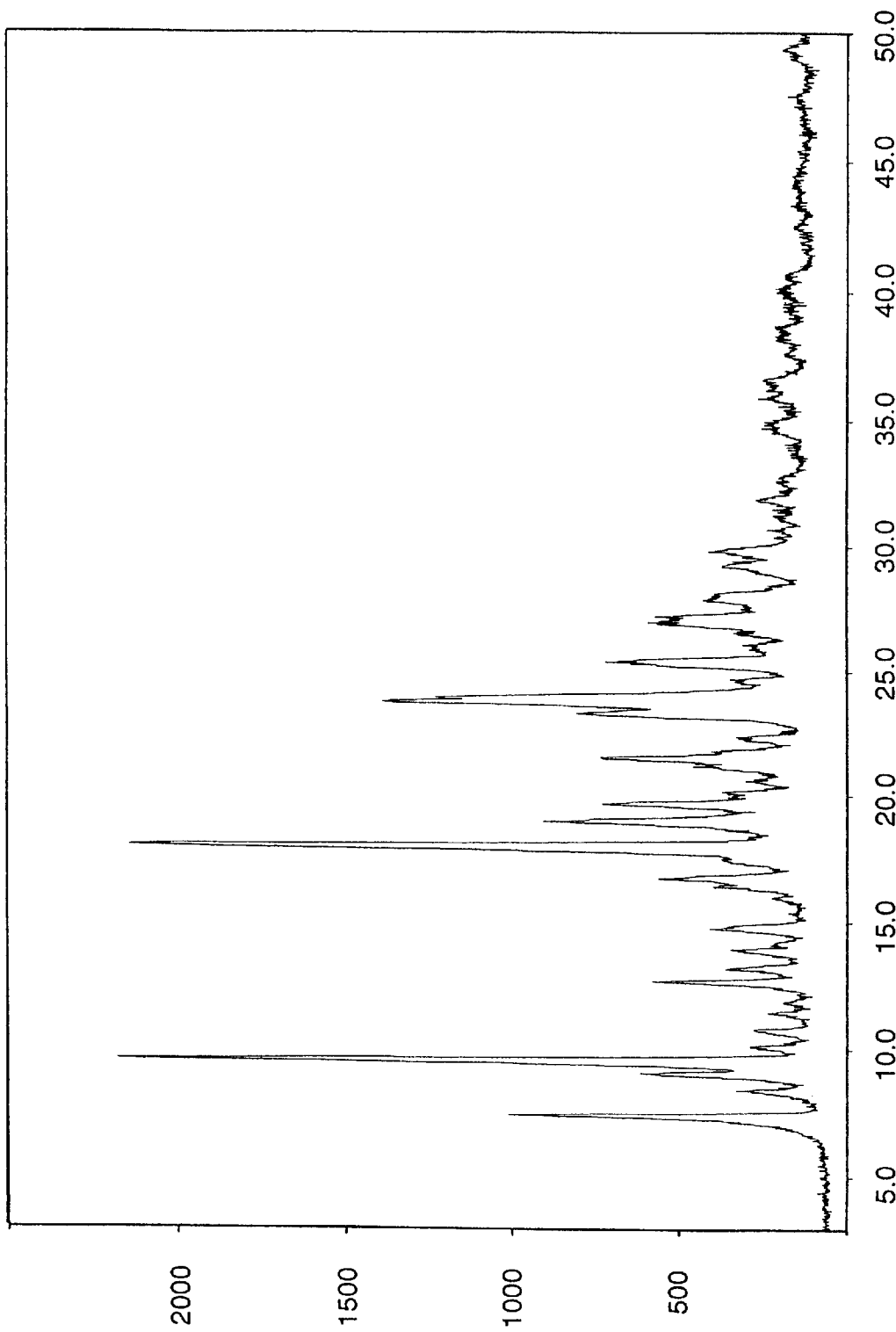
FIG. 7 shows an x-ray powder diffraction pattern of a heat treated zolpidem tartrate salt.
Figures 8A, 8B:
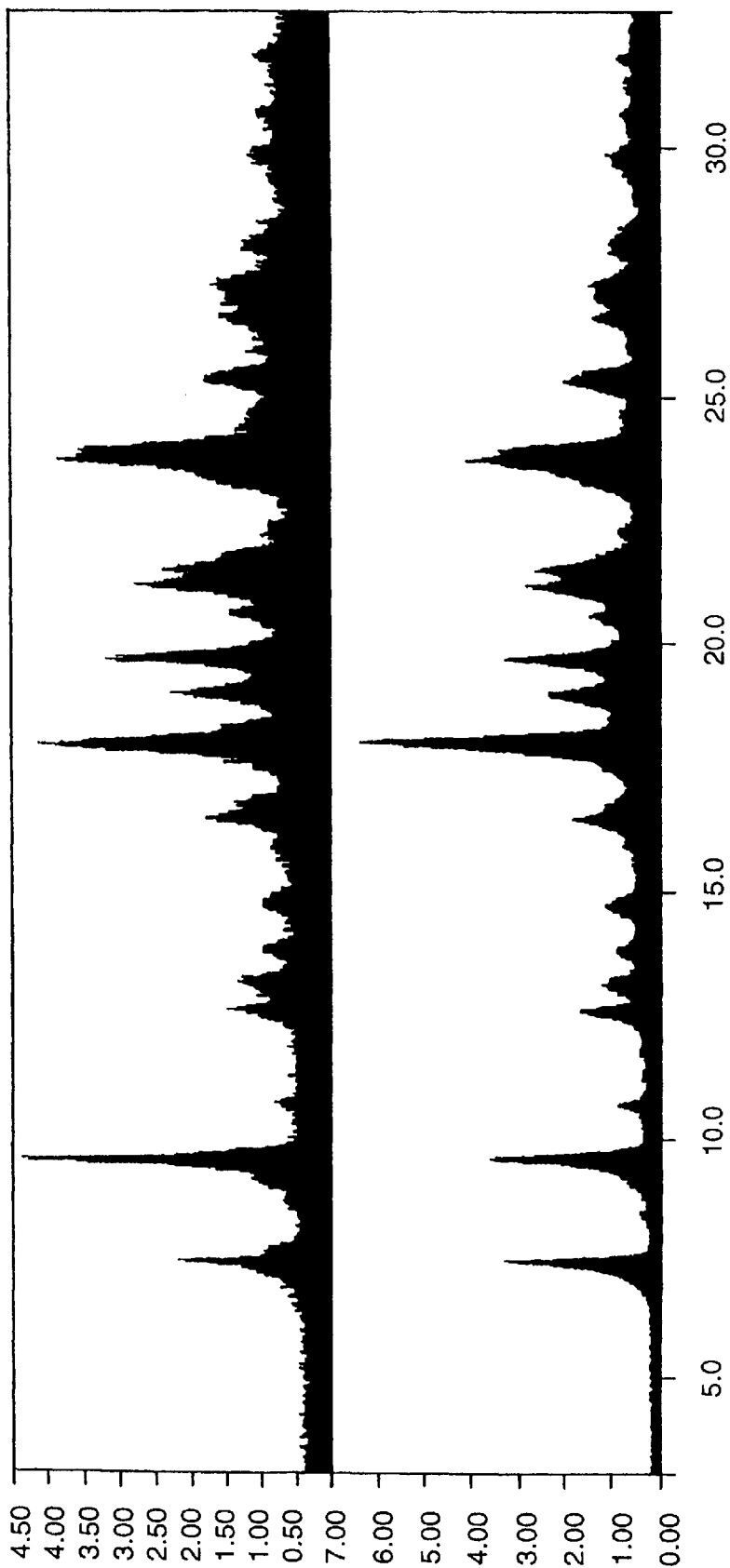
FIG. 8 shows a comparison of x-ray powder diffraction patterns for a heat treated zolpidem tartrate (graph A) and an equimolar mixture of zolpidem free base and zolpidem hydrogentartrate (graph B).

Reference 100 mg of zolpidem tartrate from Example 2 is heated over three days at 100° C. in an oil bath. After cooling, the sample is analyzed by x-ray powder diffraction and representative results are shown in FIG. 7. This heat treated product is no longer identical with zolpidem tartrate. Instead the product is identical with an artificially created equimolar mixture of zolpidem free base and zolpidem hydrogen tartrate as shown in FIG. 8. Note that graph A corresponds to the 1:1 admixed product and graph B corresponds to the heat treated product. Accordingly, heating converts the zolpidem tartrate crystal into a mixture of zolpidem hydrogentartrate and zolpidem free base.

Example 6

Amorphous Zolpidem Hydrogentartrate

Figure 9:
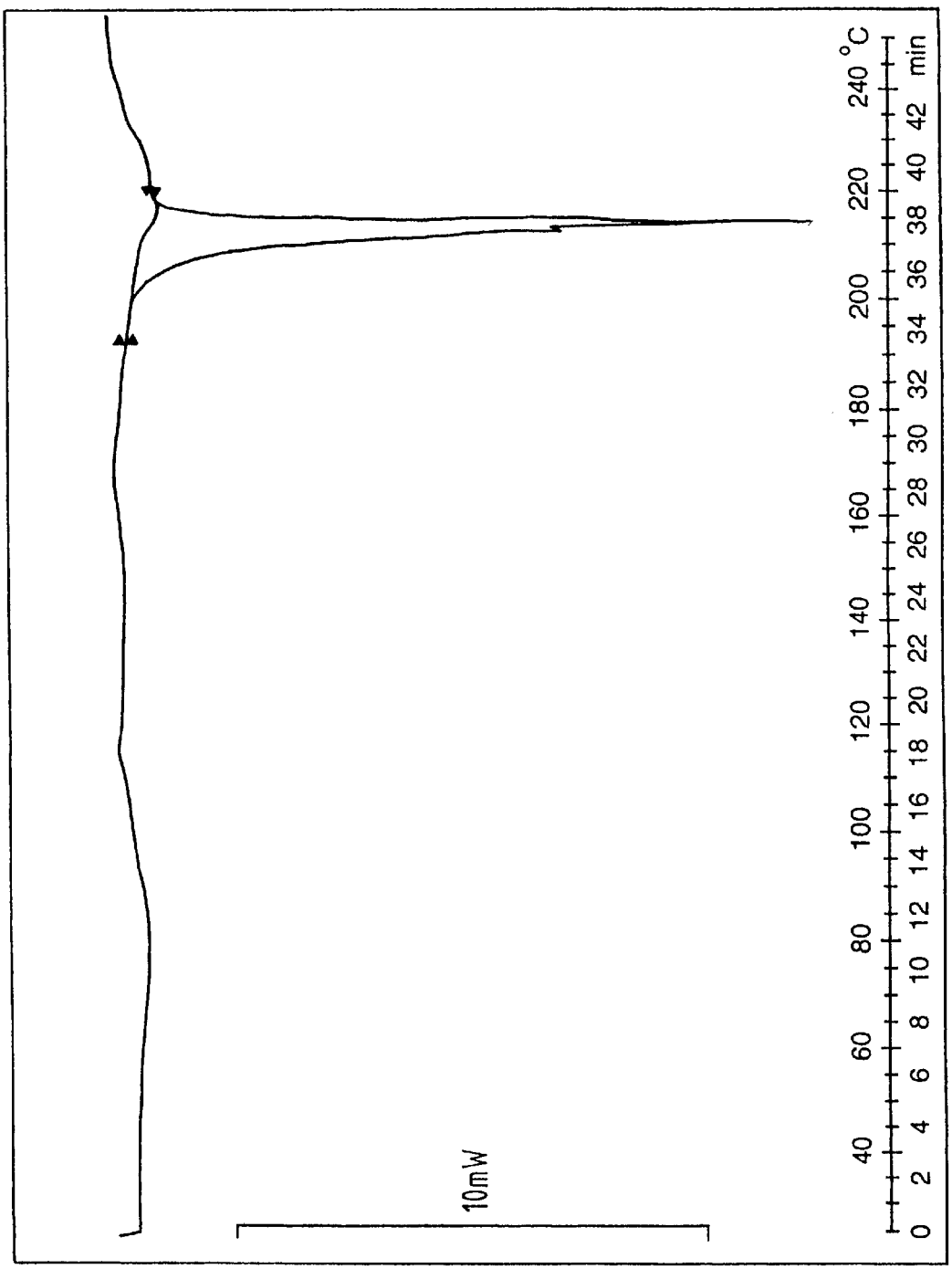
FIG. 9 shows a DSC curve for amorphous zolpidem hydrogentartrate.

A solution of 488 mg (3.25 mmol) of tartaric acid in 100 ml of water is prepared and 1.0 g (3.25 mmol) of zolpidem is added to the solution under stirring. The resulting solution is frozen at −80° C. and freeze dried. A white fluffy solid is obtained in quantitative yield and is identified as amorphous zolpidem hydrogentartrate. A representative DSC curve is shown in FIG. 9.

Example 7

Zolpidem Hydrochloride Monohydrate

Figure 10:
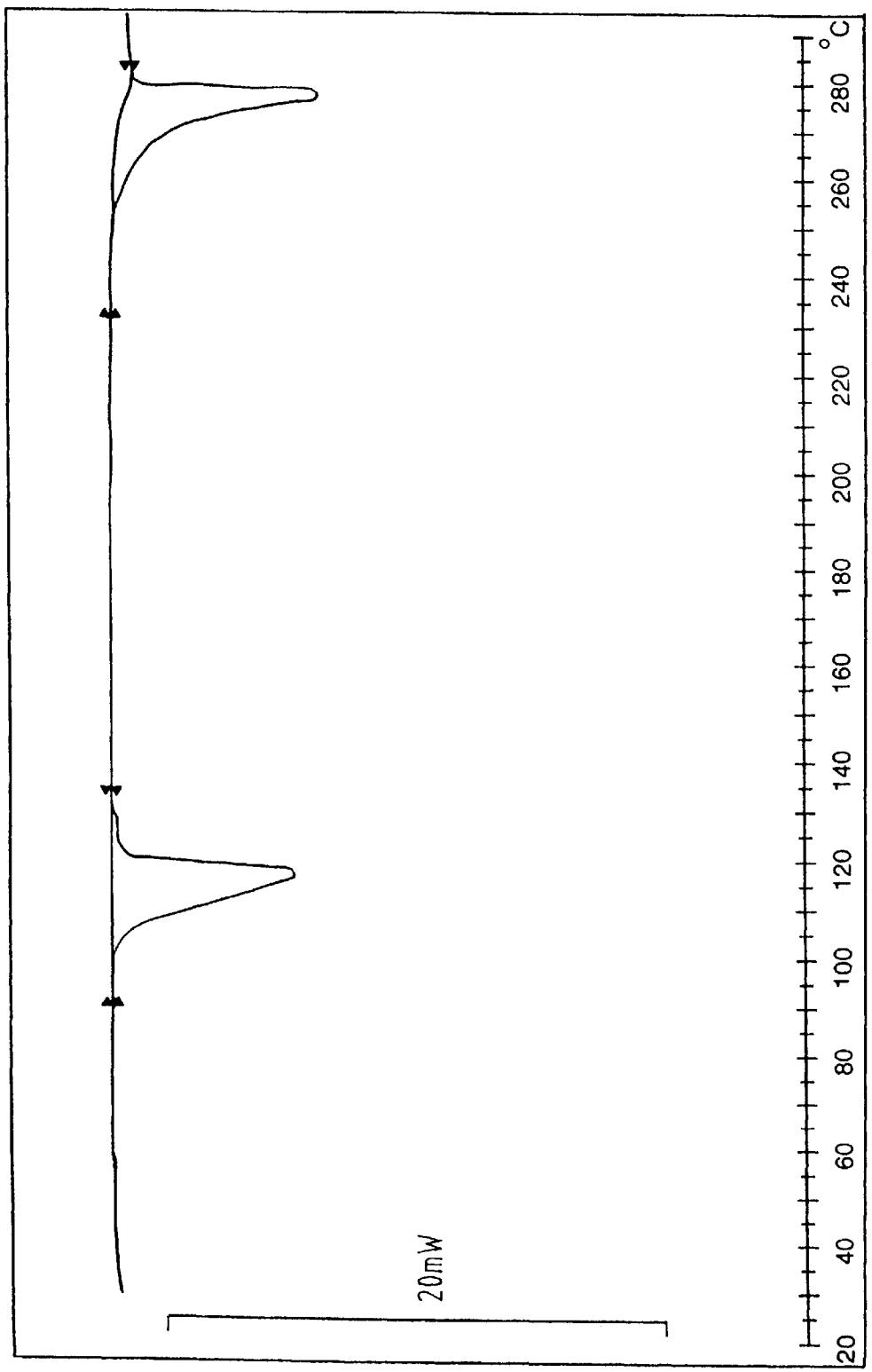
FIG. 10 shows a DSC curve for zolpidem HCl monohydrate.

One gram of zolpidem free base is added under stirring to a solution of 0.32g (a molar equivalent) of concentrated hydrochloric acid in 10 ml of acetone. The mixture is heated under stirring to 50° C. and stirred at this temperature for 30 minutes. The mixture is allowed to cool to room temperature, the formed solid is filtered off, washed with 3 ml of acetone and dried in a vacuum oven at 40° C. The amount of water, determined by thermogravimetry (TGA), corresponds to a monohydrate. A representative DSC curve is shown in FIG. 10.

Example 8

Zolpidem Hydrochloride Anhydrate

Figure 11:
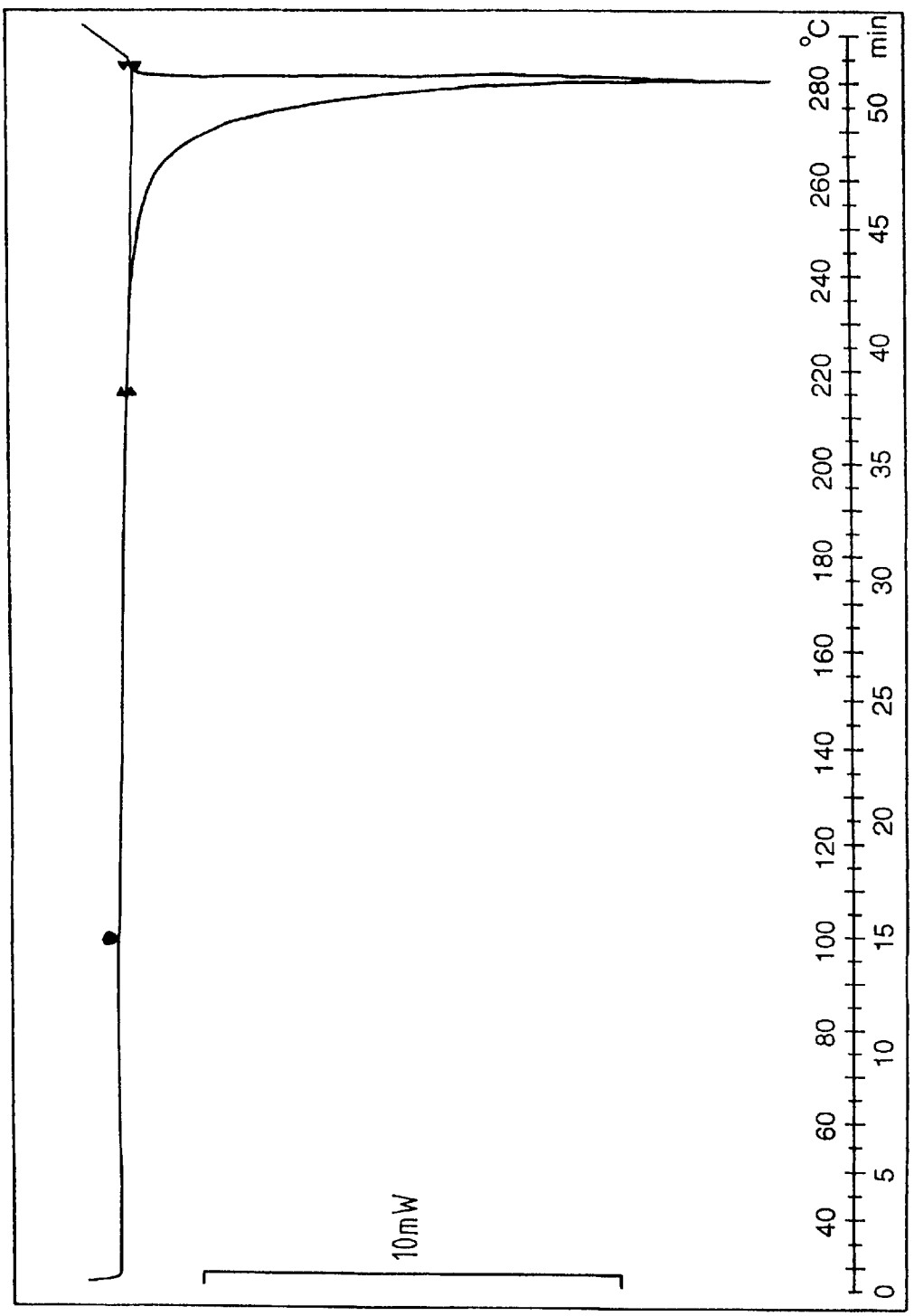
FIG. 11 shows a DSC curve for zolpidem HCl anhydrate.

One gram of zolpidem is suspended in 35 ml of 1-butanol, 0.32 g of concentrated hydrochloric acid is added and the mixture stirred 15 minutes at room temperature. The clear solution is heated to reflux and 25 ml of a water/1-butanol mixture is distilled off. The resulting mixture is allowed to cool to room temperature and stirred at room temperature for 16 hours. The formed solid is filtered off, washed with 2 ml of 1-butanol and dried in a vacuum oven at 40° C. to produce zolpidem hydrochloride anhydrate. A representative DSC curve is shown in FIG. 11.

Example 9

Zolpidem Hydrochloride Hemiethanolate

Zolpidem free base (1.0 g) is suspended in 10 ml of ethanol and heated at 50° C. until dissolution. Then, 0.32 g (molar equivalent) of concentrated hydrochloric acid is added and the solution stirred for 10 minutes. Then the bath is removed and the reaction mixture is allowed to cool to room temperature. Finally, the mixture is kept standing overnight at 4° C. The formed crystals are filtered off, washed with 3 ml of cold ethanol and dried at 40° C. in a vacuum oven to produce zolpidem hydrochloride hemiethanolate.

Example 10

Zolpidem Methanesulfonate

Figure 12:
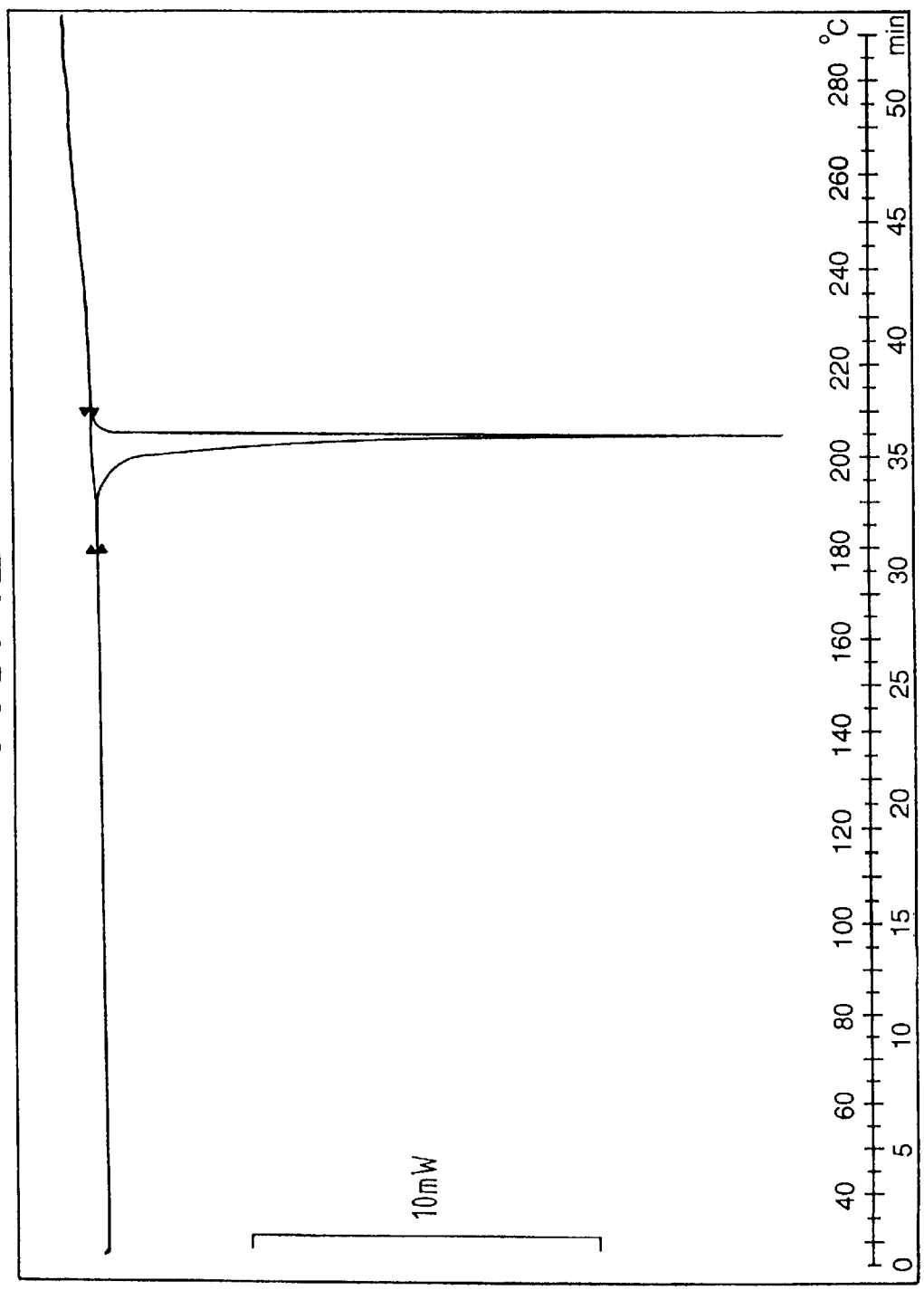
FIG. 12 shows a DSC curve for zolpidem methanesulfonate.

One gram of zolpidem free base is dissolved in 10 ml of ethanol at 50° C. Then 0.313 g (a molar equivalent) of methane sulfonic acid is added at this temperature, the mixture is stirred for 5 minutes and evaporated to dryness under reduced pressure. The residue is treated with 10 ml of acetone, the remaining solid is filtered off and washed with 5 ml of acetone and dried in vacuum oven at 40° C. to yield zolpidem methanesulfonate. A representative DSC curve is shown in FIG. 12.

Throughout this specification, the wording "tartaric acid" means naturally occurring L(+) tartaric acid. However, mutatis mutandis, the described procedures are useful also for the production of the corresponding salts of zolpidem with D- or DL-tartaric acid. The invention having been thus described, it will be obvious that the same may be varied in many ways without departing from the scope and spirit of the invention as defined by the following claims.

We claim:

1. A solid-phase zolpidem salt form having sufficient physical stability that upon heating from about 20° C. to about 250° C. at a rate of about 5° C./minute does not exhibit a melting endotherm that corresponds to zolpidem free base.

2. The zolpidem salt form according to claim 1, wherein said salt form exhibits a single melting endotherm when heated.

3. The zolpidem salt form according to claim 1, wherein said solid-phase is amorphous.

4. The zolpidem salt form according to claim 1, wherein said solid-phase is crystalline.

5. The zolpidem salt form according to claim 1, wherein said salt form is a pharmaceutically acceptable salt.

6. The zolpidem salt form according to claim 5, wherein said salt form is a salt selected from the group consisting of hydrochloride, hydrobromide, maleate, fumarate, tartrate, sulfate and sulfonates.

7. The zolpidem salt form according to claim 1, wherein the molar ratio of zolpidem moiety to anion is within the range from about 0.9–1.35:1.

8. The zolpidem salt form according to claim 7, wherein said molar ratio of zolpidem moiety to anion is about 1:1.

9. The zolpidem salt form according to claim 1, wherein said salt form is substantially free of bound water and organic solvent.

10. The zolpidem salt form according to claim 1, wherein said salt form is selected from the group consisting of zolpidem hydrogentartrate, zolpidem hydrochloride, zolpidem mesylate, zolpidem tosylate, and zolpidem sulfate.

11. The zolpidem salt form according to claim 10, wherein said salt form is zolpidem hydrogentartrate.

12. The zolpidem salt form according to claim 11, wherein said salt form is crystalline having a melting point of 203–204° C. and exhibiting a single melting exotherm under DSC analysis using 5° C./min at 203–204° C.

13. The zolpidem salt form according to claim 11, wherein said salt form is amorphous zolpidem hydrogentartrate.

14. The zolpidem salt form according to claim 10, wherein said salt form is zolpidem hydrochloride.

15. The zolpidem salt form according to claim 14, wherein said salt form is crystalline zolpidem hydrochloride monohydrate.

16. The zolpidem salt form according to claim 14, wherein said salt form is amorphous zolpidem hydrochloride.

17. A pharmaceutical composition comprising a pharmaceutically effective concentration of a zolpidem salt form as claimed in claim 1 and a pharmaceutically acceptable carrier or diluent.

18. The composition according to claim 17, wherein said composition is a solid dosage form.

19. The composition according to claim 17, wherein said zolpidem salt form is contained in an amount within the range from about 5 mg to 50 mg per unit dose.

20. A pharmaceutical composition comprising a pharmaceutically acceptable liquid carrier and having dissolved therein an effective sleep inducing amount of the zolpidem salt according to claim 1.

21. The liquid pharmaceutical composition according to claim 20, wherein said liquid carrier is an aqueous solution.

22. A method of inducing or maintaining sleep, which comprises administering an effective hypnotic amount of the zolpidem salt form as claimed in claim 1 to a mammal.

23. A method, which comprises dissolving a zolpidem salt form according to claim 1 in a solvent.

24. The method according to claim 23, wherein said solvent is a pharmaceutically acceptable carrier or diluent.

25. A zolpidem salt comprising a zolpidem moiety and an anion wherein the molar ratio of zolpidem moiety to anion is about 0.9–1.35:1.

26. The zolpidem salt according to claim 25, wherein said anion is selected from the group consisting of hydrochloride, hydrobromide, maleate, fumarate, tartrate, and sulfonates.

27. The zolpidem salt according to claim 25, wherein the molar ratio of zolpidem moiety to anion is about 1:1.

28. A zolpidem salt selected from the group consisting of zolpidem hydrochloride, zolpidem hydrobromide, zolpidem sulfate, zolpidem maleate, zolpidem fumarate, zolpidem mesylate and zolpidem tosylate.

29. A zolpidem salt selected from the group consisting of amorphous zolpidem hydrogentartrate, crystalline zolpidem hydrogentartrate anhydrate, amorphous zolpidem hydrochloride, crystalline zolpidem hydrochloride monohydrate, crystalline zolpidem hydrochloride anhydrate, crystalline zolpidem hydrochloride hemiethanoate, crystalline zolpidem sulfate, and crystalline zolpidem mesylate.

30. A method which comprises:

combining zolpidem hydrogentartrate with a zolpidem free base in molar ratio of 1:1 in methanol to form a methanolic solution having a temperature of at least 50° C.; and cooling said methanolic solution to precipitate solid zolpidem tartrate.

* * * * *